United States Patent [19]

Goldowsky

[11] 3,963,024

[45] June 15, 1976

[54] FLUID FLOW REGULATOR

[76] Inventor: Michael Goldowsky, 222 Martling Ave., Tarrytown, N.Y. 10591

[22] Filed: Apr. 8, 1975

[21] Appl. No.: 566,076

[52] U.S. Cl. .................... 128/214 R; 128/214 C; 128/214 F
[51] Int. Cl.² ........................................ A61M 5/16
[58] Field of Search ........ 128/214 R, 214 A, 214 B, 128/214 C, 214 D, 214 E, 214 F, 214.22

[56] References Cited
UNITED STATES PATENTS

| | | | |
|---|---|---|---|
| 3,512,748 | 5/1970 | Wilson | 128/214 R |
| 3,587,313 | 1/1971 | Smith | 128/214 R |
| 3,690,318 | 9/1972 | Gorsuch | 128/214 E |
| 3,756,233 | 9/1973 | Goldowsky | 128/214 C |

*Primary Examiner*—Louis G. Mancene
*Assistant Examiner*—Robert F. Cutting
*Attorney, Agent, or Firm*—Stanley J. Yavner

[57] ABSTRACT

A fluid flow regulator is inexpensively constructed in a unitary system with a rigid and transparent drip chamber overlying a rigid float chamber. The purpose of the regulator is to control the dispensing of physiological fluids or the like to be infused into the circulatory system of a patient. The unitary structure is essentially cylindrical in shape divided by a median wall into a top cylindrical portion functioning as a drip chamber and a bottom cylindrical portion functioning as a float chamber. The two chambers are connected by a pressure equalizing air tube and neither chamber is vented to the outside atmosphere. Such pressure equalization makes the system self-compensating for the purpose of maintaining a constant head for the fluid between the drip chamber and the float chamber. The float chamber includes a float which is buoyed by liquid entering the float chamber and the float and the float chamber function as a valve to selectively open and close a port leading to the infusion needle of the apparatus. The two chambers are connected by tubing which provides a flow path between the liquid in the drip chamber and the float chamber. A relatively small head is maintained across a variable restriction device in that flow path, with the arrangement providing a valve opening many times larger than the expected particulate matter size. Thus, there is no clogging over long periods of time.

9 Claims, 5 Drawing Figures

FLUID FLOW REGULATOR

This invention relates primarily to fluid flow regulators and more particularly to physiological liquid administration apparatus wherein clogging is essentially eliminated and a construction of minimum cost is presented.

Physiological fluids are normally infused into a patient with a parenteral administration set. The administration set is utilized to provide a passage between a physiological fluid in a supply container, e.g., a parenteral solution of sterile water or a saline or glucose water solution, etc. carried in a glass bottle or in a flexible plastic bag for intravenous or arterial administration. Infusion of the parenteral solution has been achieved by suspending an inverted bag above the patient and inter-connecting a length of tubing, forming a part of the administration set, to the bag by piercing a membrane stopper at the mouth of the bag with a penetrant. The tubing of prior art devices leads to a drip chamber connected in series therewith and through which the rate of solution flow could be observed. A constriction pinch valve is provided to restrict the fluid flow through the tubing to levels meeting the prescribed requirements of the patient. The free end of the tubing is connected to a hollow bore needle which is inserted into a blood vessel, e.g., a vein of the patient.

A major disadvantage encountered in the prior art administration sets is the variation that takes place relative to the rate of solution flow. Such flow rate changes can be compensated for by a technician observing the drip rate and accordingly adjusting the aforementioned constriction pinch valve. Flow rate changes are caused by either depletion of the liquid supply in the supply container, changes in blood pressure, the patient voluntarily or involuntarily raising or lowering his infusion arm, partial clogging of the infusion needle or clogging at another point in the administration set flow path. Although recent advances have been made relative to elimination of particulate matter infused into the patient by use of filters just before the needle, clogging can still occur at the constriction pinch valve.

Furthermore, minor dimensional changes in the tubing and cold flow or creeping of the prior art pinch valves has a great effect on the small flow area commonly used. Normally, the prior art tubing has an extremely small flow cross-sectional area to control the several feet of tubing pressure head. Also, the several feet of tubing used with conventional pinch valves lead to Reynold's numbers for the valve constriction in the turbulent ranges where laminar flow does not exist and very small openings are required. Such pinch valve tubing restrictions frequently clog at flow rates less than 150 cubic centimeters per hour, because it can be shown that the size opening left at the pinch valve is less than the particulate size of 10 microns, to which particles are normally filtered. Pinch valves do not permit laminar flow to develop because approximately 50 diameters of length is required to fully develop the flow. This is not achievable in point contact flow restrictors.

The above described unstable flow rate situation results primarily from the many feet of tubing used producing a relatively large head with a pinch valve taking the full head. At slow flow rates, 10 micron particles clog the pinch valve opening and even minor creeping can cause large changes in the opening. The prior art devices have attempted the substitution of silicone tubing to prevent creeping, but clogging still remained a problem not to mention that increases in system backpressure resulted in decreased flow since the devices were incapable of flow rate regulation.

Accordingly, a primary object of the present invention is to provide a fluid flow regulator apparatus, which automatically responds to changes in backpressure, to enable constant flow without clogging problems.

A further object of the present invention is to provide a fluid flow regulator which eliminates clogging problems by the use of a small head system and a flow regulator of novel construction to produce laminar flow in the system.

A still further object of the present invention is to provide a fluid flow regulator apparatus of inexpensive and yet reliable and trouble-free construction.

These and other objects of the present invention are accomplished in accordance with one illustrative embodiment of the present invention which features a fluid flow regulator for use as an administration set for the infusion of a supply liquid in a supply container into the circulatory system of a patient. The apparatus of the present invention includes a substantially cylindrical unitary structure divided by a median separator wall which is perpendicular to and substantially bisects the axis of the cylindrical structure. The median separator wall provides two chambers for the apparatus, the top or drip chamber for receiving the supply liquid in a drip-by-drip manner, and the bottom or float chamber for releasing liquid by means of a fluid valve system to the infusion needle. The two chambers are connected in the first instance by a pressure equalizing air tube which makes the system maintain a constant air pressure across the restrictor since neither chamber is vented to the outside atmosphere. In the second instance, the two chambers are connected by flexible liquid tubing which provides a passage for the liquid in the drip chamber to the float chamber. A flow restrictor device is provided in the flexible liquid tubing such that the flow rate therethrough is adjustable, so that laminar flow is provided and so that a flow rate is maintained substantially constant without adjustments.

The flow restrictor, in a preferred embodiment, includes a frame defining a substantially semi-circular passage, about which the flexible liquid tubing is wrapped, and a thumb screw for advancing a conical wedge to press the flexible tubing against the frame progressively, thereby restricting flow through the tubing in a pre-determined manner. The large effective diameter, which results at normal flow rates from the pressure by the thumb screw and wedge, is not subject to clogging because of its size relation with typical 10 micron particles, which are involved in the clogging problems experienced in prior art liquid administration sets. Likewise, minor creeping of the tubing or restrictor frame has little effect on flow rate since the effective opening left after constriction is so relatively large compared with the extremely small openings of conventional administration sets.

The above brief description, as well as further objects, features and advantages of the present invention, will be more fully appreciated by reference to the following, detailed description of the preferred, but nonetheless, illustrative, embodiment, when taken in conjunction with the accompanying drawings, wherein.

Figure 1:
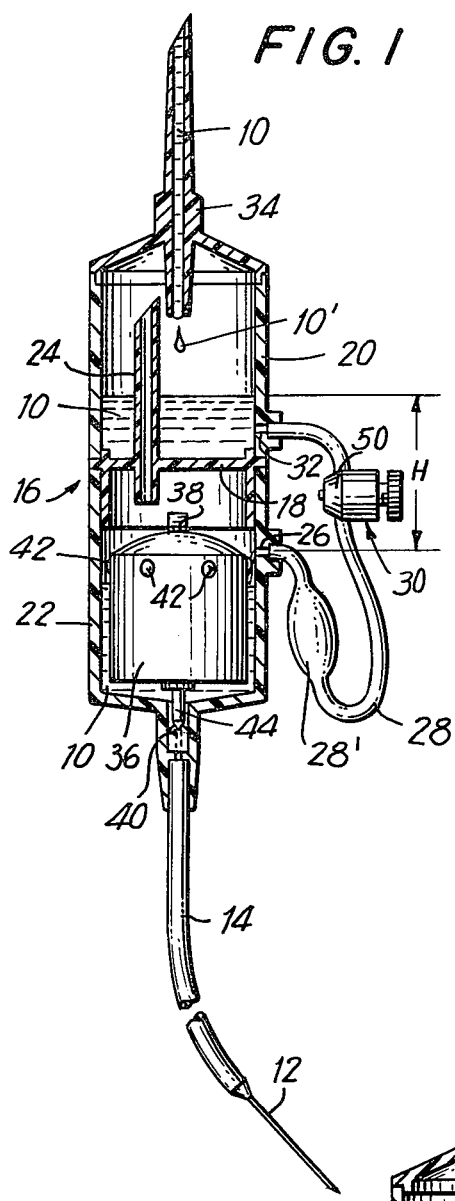
FIG. 1 is a front, sectional view of a fluid flow regulator apparatus according to the present invention, showing particularly the unitary construction including drip chamber and float chamber and the inter-connection therebetween by flexible liquid tubing, the flow through which is regulated by a flow restrictor according to the present invention.
Figure 1A:
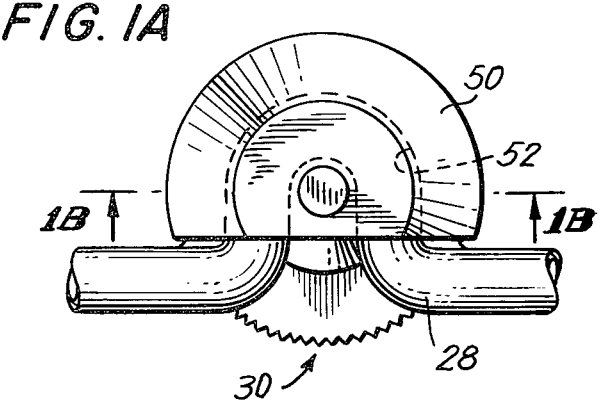
FIG. 1A is a partial, left-side view of the flow restrictor of FIG. 1 showing particularly the frame thereof and the passage defined thereby through which the flexible liquid tubing passes.
Figure 1B:
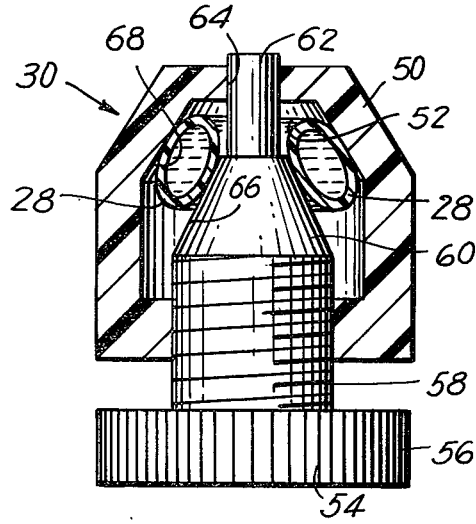
FIG. 1B is a front view of the flow restrictor of FIG. 1A, showing other features thereof.
Figure 2:
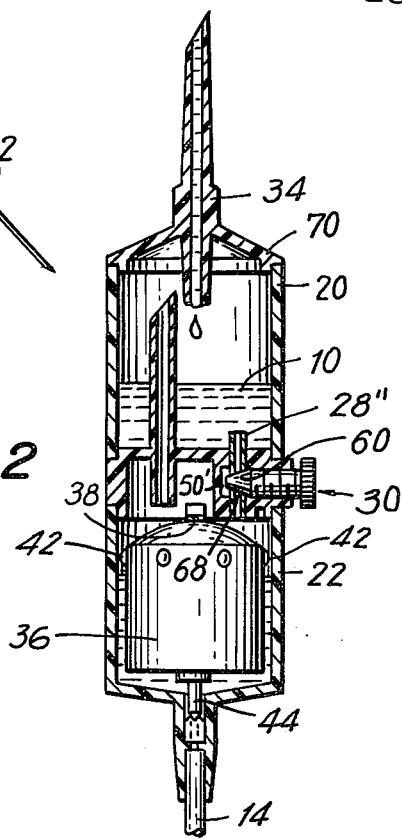
Figure 1C:
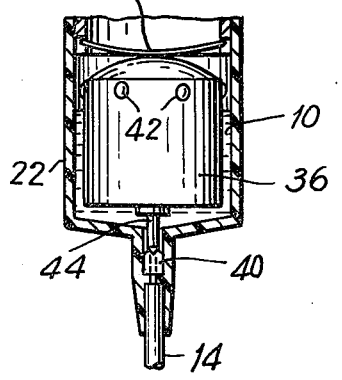

FIG. 1C is a partial, front sectional view showing particularly the float chamber portion of the fluid flow regulator apparatus of FIG. 1 and particularly the spring (shown thicker than actual size) and valve construction thereof; and FIG. 2 is a front sectional view of fluid flow regulator apparatus according to an alternative embodiment of the present invention featuring particularly the substitution of an integrally connected flow restrictor in place of the flexible liquid tubing arrangement of FIG. 1.

Figure 3A:
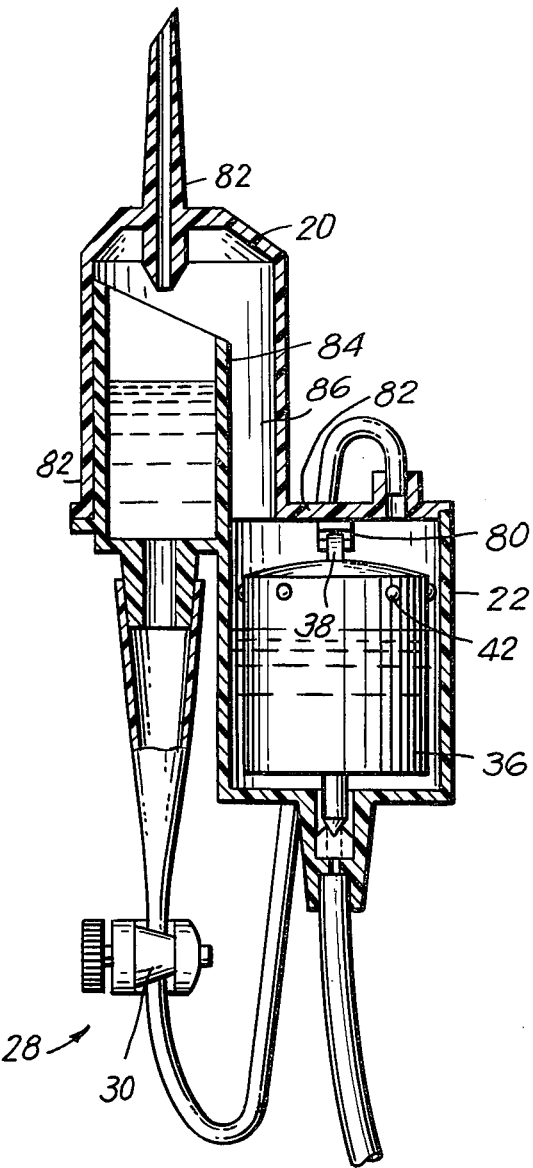
Figure 3B:
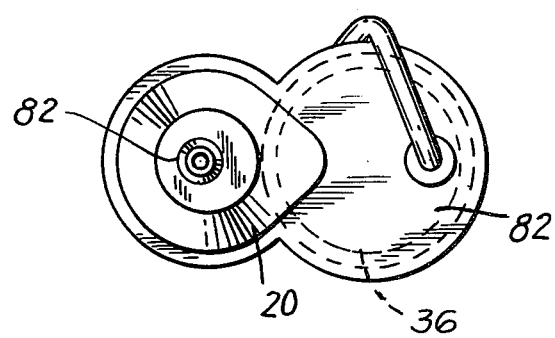

FIGS. 3A, 3B show an alternative embodiment of the present invention.

Referring to the drawings, a preferred embodiment of the present invention is illustrated in FIGS. I, 1A, 1B and 1C. Specifically, the preferred embodiment of the present invention represents a fluid flow regulator for the infusion of a supply liquid 10 from a supply container (not shown) into the circulatory system of a patient (not shown). Actual infusion takes place by means of infusion needle 12 connected by infusion tubing 14 from the fluid flow regulator, generally designated 16, of the present invention. The fluid container is either a flexible plastic bag or a vented bottle.

More specifically, the fluid flow regulator apparatus of the present invention includes a substantially cylindrical unitary structure 16 divided by a medium separator wall 18 which is perpendicular to and substantially bisects the axis of the cylindrical structure 16. Median separator wall 18 provides two portions for the cylindrical structure 16; namely, a top or drip chamer 20 and a bottom or float chamber 22. The chambers 20, 22 are connected firstly by a pressure equalizing air tube 24 for enabling the system to maintain a constant head H and neither chamber is vented to the outside atmosphere. The head H in the system shown is defined between the level of liquid 10 in drip chamber 20 and the inlet port 26 defined by float chamber 22. Also, the two chambers are connected for the flow of liquid by tubing 28, whose path is intercepted by flow restrictor 30, which, in combination with the other apparatus shown, provides a novel flow control apparatus which will not clog under normal use conditions. Bubble 28' integral with tubing 28 is used for the purposes of initially filling the drip chamber 20 to a level above outlet port 32 defined by drip chamber 20. The top of pressure equalizing air tube 24 is arranged sufficiently below the top of drip chamber 20, so as to avoid wetting thereof upon inversion of the drip chamber when replacing the supply container.

Accordingly, bubble 28' is initially squeezed which forces air into the container and when released, draws liquid into drip chamber 20 so that drip chamber 20 fills to a level above outlet port 32. Flow continues by liquid flow through penetrant 34 causing drops 10' to continue feeding liquid into drip chamber 20. Pressure equalizing air tube 24 maintains a constant ambient pressure within the two chambers which is equal to the variable head of fluid height in the supply container above the end of the drip nozzle. The level of liquid 10 in drip chamber 20 remains constant once flow leaves through exit port 40. Thus, the flow passes thru outlet port 32 and into tubing 28 with a constant driving head H for entrance to float chamber 22 by means of inlet port 26. Within float chamber 22 is a float 36 which is biased downwardly by spring 38, shown more clearly in FIG. 1C. When the supply container runs out, the level of liquid 10 decreases in float chamber 22, float 36 lowers into valve seat 40 to stop the flow of liquid into infusion tubing 14, precluding the entrance of air. This is a distinct advantage over conventional administration sets where air will automatically enter. If the device is inverted the spring holds the valve stem 44 securely in the valve seat 40 against the weight of the float, even under severe jolting.

Accordingly, for every drop out of the needle, one drop comes in from the supply to the drip chamber, which maintains a constant level of liquid in the drip chamber.

Therefore, a constant flow rate is assured in the system of the present invention by means of imposing the same air pressure across flow restrictor 30 in conjunction with a constant fluid driving head H.

Thus, it may be seen clearly that constant flow into the drip chamber is mandated by the system since the pressure head across the restrictor remains constant and indicated by the steady flow of drops 10' which may be observed by means of the transparent and rigid construction of drip chamber 20. A nurse, or another assistant, can therefore view the operation of the system by means of observing the drip rate in the drip chamber. On the other hand, the drip chamber can be made flexible and transparent with the float chamber rigid, as will be described with reference to an alternative embodiment.

It should also be mentioned that float 36 is constructed with protruding centering knobs 42 to maintain float 36 in a concentric position to insure balanced surface tension forces and smooth friction free operation. (Alternatively, inwardly directed splines can be used on the float chamber in place of knobs 42 or float 36). The correct seating of valve stem 44 is enabled by the use of a rubber valve seat 40 to provide flexibility and resilience.

Alternatively, in this preferred embodiment, bubble 28' is eliminated by use of a flexible drip chamber which is squeezed and released to initially fill drip chamber 20 with liquid 10.

At this point, a series of operational steps will be described with reference to the present invention for the purposes of clarity.

Upon detecting the requirement for fluid, the operator of apparatus according to the present invention either squeezes a flexible drip chamber or bubble 28' to initiate flow from the supply through the administration apparatus to the patient. During operation, an equilibrium of pressure is always present between float chamber 22 and drip chamber 20 by means of the connecting air tube 24. Shaking or squeezing of the supply container has minimal effect on fluid levels in this system since it is a closed system. Any increase in air pressure as would mementarily occur when the supply container is squeezed is equalized on each of air tube 24 so that the flow rate still remains constant.

In another situation, if the patient raises his infusion arm, flow rate will still remain constant. The constant flow rate is also maintained when the needle partially clogs or when the patient's blood pressure rises. In all such situations, float 36 in float chamber 22 will rise because of an increase in the level of liquid in float chamber 22. The rise in the liquid level in float chamber 22 in such circumstances is because of the constant flow into float chamber 22 even though the output flow from needle 12 is momentarily less due to the back-pressure. The rising float allows additional flow to be infused. It stops rising once the infused flow has again been equated to the float chamber inlet flow which is constant. This all occurs in a fraction of a second.

If float 36 rises beyond its equilibrium point, the level of fluid lowers in the float chamber since fluid would be infused to the patient faster than it was coming into float chamber 22. The float itself will lower until stem 44 seats and equilibrium is again established between inlet flow and outlet flow.

Referring specifically to the flow restrictor 30 shown enlarged in FIGS. 1A and 1B, it includes a frame 50 structured to define a substantially semi-circular passage 52 through which is placed tubing 28 for the purpose of controlling flow therethrough. Threadably attached to frame 50 is a thumb screw, generally designated 54, which includes knurled handle 54, threaded portion 58, tapered wedge 60 and stem 62. Stem 62 protrudes outwardly of frame 50 through support bearing 64 defined thereby. Tapered wedge 60 defines tapered side walls 66, substantially parallel to wedge wall 68 defined by frame 50.

Control of flow through tubing 28 is accomplished and enabled by means of the large 180 degree squeezed down length of tubing 28, which offers substantial advantages over a point contact control. In the design of the present invention, the flow restrictor 30 operates over a relatively large squeezed down length L of tubing 28 in the direction of flow. L is equal to $(\pi D)/2$ where $D$ is the mean diameter of the fluid passageway after being wrapped 180° around tapered wedge 60. A typical diameter of fluid passageway is five-sixteenths of an inch so that L equals at least ½ inch, which is large compared to conventional valves. This long length compared to the size opening left during use is so large that laminar flow is developed. The resulting laminar flow at normal flow rates creates a large flow resistance with a large size opening B, remaining after significantly squeezing down flow restrictor 30. B is large enough so that it will not be clogged by typical 10 micron particles and its dimensional stability gives excellent long term, stable operation.

Considering Q to be the flow rate in cubic inches per second, $\Delta P$ to be the pressure drop (due to head $H$) in pounds per square inch, $A$ and $B$ ($B$ being the lesser by far) to be the effective width and height in inches, respectively, of the opening left after significantly squeezing down tubing 28, $u$ to be the fluid viscosity in pound-seconds per square inch, the opening can be calculated as follows considering typical values such as L equals 0.5, A equals 0.125, $u$ equals $1.5 \times 10^{-7}$ (for water or low glucose concentrations) and Q equals $1.7 \times 10^{-3}$ for typically 100 cubic centimeters per hour flow rate:

with a 1 inch head ($H$)

$$B^3 = \frac{12 \, uLQ}{A \, \Delta P} = 3.4 \times 10^{-7}$$

$$B = 0.007 \text{ inch} = 175 \text{ microns}$$

Thus, the smallest opening left in the tubing is more than 17 times greater than the 10 micron typical particulate size in the parenteral fluid after filtering. No clogging is possible and flow remains stable even at very slow flow rates, due to the low head used and the long length of tubing squeezed down as compared with the relatively short length squeezed down by typical pinch valve constructions In conventional drip sets, the pinch valve is used on approximately 6 feet of tubing and acts like a flow orifice, since the flow path does not have sufficient length to develop laminar flow through the large pressure difference. In the prior art, this flow can be shown to act in a turbulent manner at normal rates when several feet of fluid head exist because the Reynold's number is approximately 7,000 at a typical flow rate as compared to a Reynold's number of about 500 in a device according to the present invention at the same flow rate. It is generally known that flow is laminar only up to approximately 2,300. The standard pinch valve flow is governed by the following equation:

$$Q = C_D BA \sqrt{\frac{2 \Delta P \, g}{d}}$$

where:
 $C_D$ = discharge co-efficient, 0.61 typically
 $g$ = gravity = 384 inches/seconds$^2$
 $d$ = fluid density = 0.036 pounds/inches$^3$ for water
 $Q$ = $1.7 \times 10^{-3}$ (as in the previous example)
 $\Delta P$ = 2.6 psi (pressure head due to 6 ft. of infusion tubing)

$$B = \frac{Q}{C_D A} \sqrt{\frac{d}{2 \Delta P \, g}} = .0001 \text{ inches} = 2.5 \text{ microns}$$

The 2.5 microns opening is much less than the possible 10 microns particulate matter size in the fluid. The valve in prior art pinch valve constructions is predicted to readily clog. This is true even when creep is eliminated by the use of silicone tubing. Furthermore, the use of particulate filters, normally used near the exit of the set before the needle, provides no relief from this situation.

According to the present invention, the conical shape of inner wedge wall 68 at the top of frame 50, in conjunction with support bearing 64 which prevents the thumb screw 54 from bending and insures a rigid restraint for tubing 28, provides dimensional stability. Minimal creeping of tubing 28 or frame 50 therefore has practically no effect, particularly in view of the large effective opening provided by a flow restrictor of the present invention. The equations presented above graphically illustrate such advantages in the opening left when tubing is squeezed down using the flow restrictor of the present invention compared to the small openings of squeezed down tubing in conventional pinch valve drip sets. The small head of approximately 1 inch used by means of the present invention enables laminar performance and relatively large openings of typically 175 microns remaining after the tubing is squeezed down. The squeeze-down stresses induced in the tubing are also lower resulting in less creep or cold flowing of the material as well.

Referring now to the alternative embodiment of FIG. 2, a construction is shown whereby penetrant 34 is constructed in the form of a cap 70 which is flanged at its edges to fit conveniently over the top of drip chamber 20. Furthermore, drip chamber 20 can be either rigid or flexible as discussed with reference to the preferred embodiment, but if rigid, an eye-dropper squeezer (not shown) can be inserted into the wall of drip chamber 20 for the purposes of replacing either a flexible drip chamber or bubble 28' for initial filling. In this way, an integral construction is enabled whereby flow restrictor 30 is integrally related in a unitary construction with float chamber 22. As FIG. 2 illustrates, the construction of flow restrictor 30 is similar and functionally the same as the flow restrictor shown in FIGS. 1A and 1B. Tubing 28'' is wrapped around tapered wedge 60 is the same way as for the preferred embodiment. Wedge wall 68, internally defined by frame 50, may be considered the same even though not shown as clearly in FIG. 2 as wedge wall 68 illustrated in FIGS. 1A and 1B. Tubing 28'' thereby communicates between liquid 10 in drip chamber 20 and float chamber 22 with intermediate control by flow restrictor 30.

Thus, a completely rigid construction for both drip chamber 20 and float chamber 22, with or without centering knobs 42 on float 36, is enabled in all embodiments of the present invention. This leads to a construction of greatly reduced cost, laminar flow in all practical conditions of use because of the small head H and the construction of flow restrictor 30, and yet an adjustable flow pattern which is maintained constant without the need for continuous adjustment. Such a construction offers distinct advantages over presently available administration sets which suffer clogging problems due primarily to pinch valves operating on a small length of tubing, with use of several feet of pressure head and with creeping problems with respect to valve body or tube motion and resulting turbulent flow which is undesirable in creating small constriction areas for use and control of administration sets. Furthermore, the large head typically used in prior art devices leads to other problems, particularly when it is considered that six feet of tubing is used in presently available drip sets. Also, prior art devices do not have the capability of regulating or maintaining a constant rate of flow with increases or decreases in flow backpressure. A simple occurrence such as the needle pressing against the wall of a vein has been known to reduce flow in prior art devices.

It should also be mentioned that the present invention contemplates an alternative embodiment featuring the same construction as that shown in FIG. 1, but with the chambers vertically split, except, of course, for the penetrant 34 and float 36. Such a two-piece construction is inexpensive as is the preferred embodiment of the present invention, but further enables assembly and packaging conveniences which might suit particular applications more readily.

As further construction conveniences, float 36 can be formed of rigid polyurethane foam with knobs 42 and valve stem 44 integrally molded and tubing 28 is readily available with bubbles 28' integrally formed.

As a still further alternative embodiment (FIGS. 3A, 3B), the apparatus of the present invention includes a drip chamber 20, a float chamber 22 and flow means 28 interconnecting the chambers with a flow restrictor 30 as part of the flow means, as hereinbefore described. However, instead of arranging the float chamber 22 directly below the drip chamber 20 and separated by a median wall 18 with an air tube connection (FIG. 1), the float chamber 22 is laterally displaced, in one dimension only, with the spring 38 held in place at its ends by legs 80 depending from a broader combination top cap and penetrant 82. The penetrant is laterally displaced in the top cap from the depending legs 80 by an amount approximately equivalent to the displacement of the float chamber 22 from the drip chamber 20 as discussed above. This places the penetrant above the drip chamber 20 and the spring holding legs 80 above the float chamber 22. The separation between float chamber and drip chamber in this embodiment is accomplished by an upstanding wall 84 or other separating means which rises from the bottom of the drip chamber 20 to a point below the top cap 82, so that air pressure equalization is provided by a common ambient space 86 above the float and above the liquid in the drip chamber. This construction thereby eliminates the need for pressure equalization air tube 24 (FIG. 1) previously described. Thus, an embodiment is provided which is a simple, two piece construction easily assembled to insure the functioning intended.

In all constructions of the present invention, tests have proven the advantages cited and thus, the present invention offers superior performance as presented in the foregoing specification. Furthermore, it should also be understood that replacement in the present invention of flow restrictor 30 by a pinch valve of standard construction will still result in greatly improved performance considering flow regulating capability, particularly.

What is claimed is:

1. An administration set for the infusion of a supply liquid in a supply container into a separate liquid system comprising means for forming an access for liquid flow from said supply container, a combined drip chamber and float chamber apparatus defining drip and float chambers, said float chamber for regulating flow, a means separating said chambers, a pressure equalizing means connecting said chambers and flow means for establishing an adjustable liquid flow between said chambers.

2. The invention according to claim 1 wherein said flow means includes a flow tube and a flow restrictor having a frame defining a substantially semi-circular passage for said flow tube and a movable conical wedge for pressing said flow tube against said frame to restrict flow of liquid therethrough.

3. The invention according to claim 1 wherein said apparatus is substantially of cylindrical shape with said wall being approximately perpendicular to its axis and substantially bisecting said cylindrical shape and with said chambers being sealed from ambient pressure outside said apparatus.

4. The invention according to claim 2 wherein said float chamber defines an opening for receiving said flow tube and said apparatus and flow means are constructed to maintain a constant pressure head between a liquid level within said drip chamber and said opening.

5. The invention according to claim 1 wherein said flow means includes means for initially filling said drip chamber with said liquid.

6. The invention according to claim 1 wherein said flow means includes a flow tube and a flow restrictor, said flow restrictor being integrally constructed with said apparatus.

7. The invention according to claim 1 wherein said flow means includes tubing and a flow restrictor comprising means for squeezing a sufficiently long length of said tube to establish laminar flow.

8. The invention according to claim 1 wherein said flow means includes a flow tube and a flow restrictor for squeezing down said flow tube to establish a desired rate of flow.

9. An administration set for the infusion of a supply liquid in a supply container into a separate liquid system comprising a flow tube and a flow restrictor including a frame defining a substantially semi-circular passage for said flow tube and a movable conical wedge for pressing said flow tube against said frame to restrict flow therethrough by squeezing a sufficiently long length of said flow tube to establish laminar flow.

* * * * *